(12) United States Patent
Taff et al.

(10) Patent No.: US 10,926,094 B2
(45) Date of Patent: Feb. 23, 2021

(54) BI-VENTRICULAR IMPLANTABLE MEDICAL DEVICE

(71) Applicant: BIOTRONIK SE & CO. KG, Berlin (DE)

(72) Inventors: Brian M. Taff, Portland, OR (US); Hannes Kraetschmer, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 276 days.

(21) Appl. No.: 15/807,627

(22) Filed: Nov. 9, 2017

(65) Prior Publication Data
US 2018/0140847 A1 May 24, 2018

Related U.S. Application Data

(60) Provisional application No. 62/426,233, filed on Nov. 24, 2016.

(51) Int. Cl.
*A61N 1/365* (2006.01)
*A61N 1/368* (2006.01)
(Continued)

(52) U.S. Cl.
CPC ....... *A61N 1/36521* (2013.01); *A61N 1/3688* (2013.01); *A61N 1/36842* (2017.08); *A61N 1/36843* (2017.08); *A61N 1/025* (2013.01); *A61N 1/368* (2013.01); *A61N 1/3627* (2013.01); *A61N 1/36542* (2013.01); *A61N 1/36564* (2013.01); *A61N 1/36571* (2013.01); *A61N 1/36578* (2013.01); *A61N 1/37252* (2013.01); *A61N 1/39622* (2017.08)

(58) Field of Classification Search
CPC ............ A61N 1/36842; A61N 1/36843; A61N 1/3688; A61N 1/36521
See application file for complete search history.

(56) References Cited

U.S. PATENT DOCUMENTS

| | | |
|---|---|---|
| 5,800,467 A | 9/1998 | Park et al. |
| 7,627,374 B1 | 12/2009 | Farazi et al. |
| 2013/0218222 A1 | 8/2013 | Doerr |

OTHER PUBLICATIONS

M. R. Ginks et al. "Relationship between intracardiac impedance and left ventricular contractility in patients undergoing cardiac resynchronization therapy", EUROPACE vol. 13, No. 7, Apr. 15, 2011 (Apr. 15, 2011), pp. 984-991, XP055052815, ISSN: 1099-5129, DOI10.1093/europace/eur055.

(Continued)

*Primary Examiner* — Joseph M Dietrich
(74) *Attorney, Agent, or Firm* — Laurence A. Greenberg; Werner H. Stemer; Ralph E. Locher

(57) ABSTRACT

A biventricular (BiV) implantable cardiac stimulator contains a stimulation control unit, one or more stimulation units, an impedance measurement unit and an impedance evaluation unit. The stimulation control unit is operatively connected to one or more stimulation units to control delivery of stimulation pulses by the one or more stimulation units. The stimulation control unit is configured to assess ventricular contractility based on an impedance signal generated by the impedance evaluation unit and to switch between at least a univentricular left ventricular stimulation mode and a biventricular stimulation mode and to evaluate the ventricular contractility in relation to the respective ventricular stimulation mode.

14 Claims, 10 Drawing Sheets

(51) Int. Cl.
    *A61N 1/372*     (2006.01)
    *A61N 1/02*     (2006.01)
    *A61N 1/39*     (2006.01)
    *A61N 1/362*     (2006.01)

(56) References Cited

OTHER PUBLICATIONS

R. Dustan Sarazan et al.: "Left ventricular pressure, contractility and dp/dtmax in nonclinical drug safety assessment studies" Journal of Pharmacological and Toxicological Methods, vol. 66, No. 2, Sep. 1, 2012 (Sep. 1, 2012), pp. 71-78, XP055436940, US ISSN: 1056-8719, DOI:10.1016/j.vasc.2012.05.009.

BI-VENTRICULAR IMPLANTABLE MEDICAL DEVICE

CROSS-REFERENCE TO RELATED APPLICATION

This application claims the priority, under 35 U.S.C. § 119(e), of provisional patent application No. 62/426,233 filed Nov. 24, 2016; the prior application is herewith incorporated by reference in its entirety.

BACKGROUND OF THE INVENTION

Field of the Invention

The invention refers to a biventricular implantable cardiac stimulator containing a stimulation control unit, one or more stimulation units, an impedance measurement unit and an impedance evaluation unit. The stimulation control unit is operatively connected to one or more stimulation units to control delivery of stimulation pulses by said one or more stimulation units.

Implantable cardiac stimulators in the form of cardiac pacemakers or cardioverters/defibrillators are common in the field of art. Such cardiac stimulators are generally connected to electrode leads, which have stimulation electrodes, and optionally include additional defibrillation electrodes, in a ventricle of a heart or in the direct vicinity thereof. Via a stimulation electrode, a cardiac pacemaker can deliver an electrical stimulation pulse to the muscle tissue of a ventricle, so as to evoke a stimulated contraction of the ventricle, provided that the stimulation pulse is sufficiently intense and the heart muscle tissue (myocardium) is not presently in a refractory phase. Within the scope of this description, such a stimulated contraction of a ventricle is referred to as a stimulated event, and a stimulation pulse that has sufficient intensity to evoke a stimulated contraction of a ventricle is referred to as "suprathreshold". When a natural contraction of the ventricle occurs, it is referred to as an intrinsic activity, or as a natural or intrinsic event, within the scope of this description. A contraction of the right atrium of a heart, for example, is referred to as an atrial event, which can be a natural atrial event, for example, or—in the case of an atrial cardiac pacemaker—a stimulated atrial event. Similarly, a distinction can be made between natural (intrinsic) and stimulated left-ventricular and right-ventricular events.

Starting from the excitation site, a local excitation of the myocardium spreads in the myocardium by way of stimulus conduction and results in a depolarization of the muscle cells, and hence in a contraction of the myocardium. After a short time, a repolarization of the muscle cells occurs, and hence a relaxation of the myocardium. During the depolarization phase, the myocardium cells are not receptive to excitation, as they are refractory. The period is referred to as a refractory period. Electrical potentials accompanying the depolarization and repolarization can be detected and the temporal curves thereof—an electrocardiogram—can be evaluated.

An electrocardiogram (ECG) is a recording of electrical activity of the heart, wherein in a typical ECG trace, the QRS-complex represents contraction of the ventricles due to depolarization of the myocardial cells, while the repolarization of the myocardial cells accompanying the relaxation of the myocardium is reflected in a T-wave.

In healthy people, the respective cardiac rhythm is determined by a sinoatrial node controlled by the autonomic nervous system. By way of stimulus conduction, the sinoatrial node excites the right atrium of a human heart, and an AV node excites the (right) ventricle of the heart. A natural heart rhythm originating from the sinoatrial node is therefore also referred to as a sinus rhythm and results in respective natural contractions of the respective ventricle that can be detected as natural (intrinsic) events.

Such natural (intrinsic) events are detected by measuring the electrical potentials of the myocardium of the respective ventricle using sensing electrodes that are part of a corresponding electrode lead. The sensing electrodes can also be the stimulation electrodes and be used alternately as stimulation and as sensing electrodes. Sensing—for example the perception of intrinsic events—is typically carried out by a sensing electrode pair, which is formed by two adjoining electrodes, more specifically a tip electrode and a ring electrode, of which the tip electrode is also used as the stimulation electrode. In this way, a bipolar measurement of an intracardiac electrocardiogram (IEGM) is obtained. Furthermore, unipolar measurement of the IEGM are typically performed using the tip electrode as measurement electrode and the casing of the implantable cardiac stimulator as return electrode. The sensing and the stimulation in the ventricle take place with the aid of a ventricular electrode lead and the stimulation and the sensing in the atrium (in the right atrium) take place with an atrial electrode lead, that are connected separately to the respective cardiac stimulator. Additionally, a left-ventricular electrode lead may be provided, that typically routes through the coronary sinus and affiliated branching veins to wrap around the left ventricle. The left-ventricular electrode lead can contain a small-surface-area stimulation and/or sensing electrode.

With respect to the terms used herein, it shall be pointed out that within the scope of this text the terms stimulation electrode or sensing electrode refer to a respective electrode pole on an electrode lead, wherein stimulation pulses are delivered or electrical potential is measured. It is also being pointed out that it is also customary to refer to an electrode lead used for stimulation as a "stimulation electrode".

During operation of the cardiac stimulator, the sensing electrodes are connected to corresponding sensing units, which are configured to evaluate a respective electrocardiogram recorded using a sensing electrode (or a sensing electrode pair) and in particular to detect intrinsic atrial or ventricular events; natural atrial or ventricular contractions. This is done, for example, by a threshold comparison, wherein an intrinsic event is detected when a respective intracardiac electrocardiogram exceeds a suitably predefined threshold.

The respective intrinsic atrial heart rate (atrial frequency) or ventricular heart rate (ventricular frequency) can be derived from the frequency at which the atrial or ventricular events follow each other, and tachycardia, for example, can thus be detected.

In typical demand pacemakers, the detection of natural events is also used to suppress (inhibit) the delivery of stimulation pulses to a corresponding ventricle, if the natural event is detected during a time window prior to the planned delivery of a stimulation pulse to the ventricle. In rate-adaptive cardiac pacemakers, the time at which a respective stimulation pulse is delivered is scheduled as a function of a respective stimulation rate, corresponding to the physiological need of a patient. For example, with a greater exertion level of the patient, physiological need increases and a higher output rate of the pacemaker is required. For this purpose, a cardiac stimulator can be equipped with one or more activity sensors, which can be a CLS sensor, for example, which will be described in more detail hereafter.

The natural effect of the autonomic nervous system on the heart rate, which is reproduced by a rate-adaptive cardiac stimulator, is referred to a chronotropy.

In addition to the chronotropy, the cardiac performance is also determined by the contractility of the heart, referred to as inotropy.

To determine the contractility of a heart, it is typical to arrange an impedance or conductivity measuring unit in a housing of a cardiac stimulator (for example an implantable cardiac pacemaker). The unit is configured to generate a unipolar or bipolar impedance or conductivity curve signal. For this purpose, several impedance or conductivity values are measured, or a corresponding impedance or conductivity curve is measured, during at least one cardiac cycle. This is done either in a unipolar or in a bipolar manner as previously described. Moreover, an evaluation unit is arranged in the housing, to evaluate the impedance or conductivity response and derive a contractility value from the impedance or conductivity response. Electrotherapy devices, which are able to determine the contractility of a heart, provide the option to adapt a therapy to be delivered by the electrotherapy device to the respective contractility state of the heart of the patent.

As indicated above, the contractility describes the inotropic state of a heart. The contractility influences the force and speed of a myocardial contraction. Contractility is controlled by three mechanisms:
a) direct control by the autonomic nervous system (ANS),
b) the so-called Frank-Starling mechanism, and
c) the so-called Bowditch effect (force-heart rate coupling).

The primary mechanism, controlling the circulatory system regulation through the autonomic nervous system, increases the contractility and the heart rate when an increased metabolic need exists, for example during physical exertion, so as to ensure suitable blood supply. In healthy people, the inotropy of the heart thus causes a rise in the contractility due to increased physiological demand.

In patients with chronic heart failure (HF), the myocardial contractility decreases to a low level and the interventricular synchronization worsens. This is accompanied by a low ejection fraction (EF) as well as by a low quality of life and high mortality. HF is common among the population. Some HF patients are treated with resynchronization therapy devices, for example 3-chamber cardiac pacemakers or defibrillators. The objective of such a therapy is to synchronize the two ventricles of a heart by way of biventricular stimulation so as to improve the time response of the ventricles and consequently cardiac performance. Such a therapy is also referred to as cardiac resynchronization therapy (CRT).

Cardiac resynchronization therapy (CRT) is a special form of the more general cardiac rhythm management (CRM), which also includes, for example, simple stimulation of only one ventricle to treat bradycardia. A CRM stimulator can therefore also be a single-chamber cardiac pacemaker.

Because the contractility of the heart can be controlled physiologically by the autonomic nervous system, the detection of the contractility can also be utilized to adjust a physiologically adequate stimulation rate in rate-adaptive cardiac pace-makers. This type of stimulation rate control, as addressed above, is also known as closed loop stimulation (CLS).

For CLS, the intracardiac impedance response after the start of the ventricle contraction is measured. This measurement is carried out both for intrinsic and for stimulated events. There is a direct dependency between the right-ventricular impedance response and the contraction dynamics. The contraction dynamics, in turn, is a parameter for the stimulation of the heart by the sympathetic nervous system.

Closed loop stimulation is, as mentioned above, the control of the stimulation rate with a rate-adaptive cardiac pacemaker.

Closed loop stimulation (CLS) facilitates rate adaptation in CRM implants. This rate adaptation tracks patient metabolic demand and psychological stress condition and is emergent from continuous measurements of myocardial contractility. In general clinical terms, dP/dt assessments operate as the dominant translatable metric for grading such contractility. Further, the efficacy of patient/implant interactions, especially in the context of CRT therapies, is optimally configured in cases where LV dP/dt (and hence contractility) can be maximized on a beat-by-beat basis.

Alternative approaches for assessing myocardial contractility in a continuous fashion, i.e. using implantable pressure sensors, within CRM therapeutic devices have been suggested but never materialized into a product. So far, the only means for monitoring dP/dt conditions demands the use of either cardiac catheterization (and direct invasive clinical interaction) or interpretive methods where echocardiographic imagining is used to create surrogate assessments of contractile response.

SUMMARY OF THE INVENTION

It is an object of the invention to provide an improved biventricular implantable cardiac stimulator.

According to the invention, the object is achieved by a biventricular implantable cardiac stimulator containing a stimulation control unit, one or more stimulation units and a contractility determination unit that is configured to generate a contractility signal that reflects myocardial contractility. The stimulation control unit is operatively connected to one or more stimulation units to control delivery of stimulation pulses by said one or more stimulation units. The stimulation control unit is configured to switch between at least a univentricular left ventricular stimulation mode and a biventricular stimulation mode and to evaluate the ventricular contractility in relation to the respective ventricular stimulation mode.

According to an embodiment of the present invention, the contractility determination unit is configured to perform a contractility evaluation of the contractility signal automatically. The stimulation control unit is configured to switch between the univentricular left ventricular stimulation mode and the biventricular stimulation mode according to the result of the contractility evaluation.

Preferably, the contractility determination unit is configured to perform the contractility evaluations in a periodical manner.

In an embodiment of the present invention, the contractility evaluation is based on a comparison of the contractility signal with predetermined templates. The templates include at least one template representing cardiac contractility values in univentricular left ventricular stimulation mode and one template representing cardiac contractility values in biventricular stimulation mode. Preferably, the templates comprise cardiac contractility values depending on heart rate.

Preferably, according to an embodiment of the present invention, the stimulation control unit is configured to determine the templates according to the contractility evaluations, wherein the templates are updated in a periodical manner.

For instance, the templates can be determined regulary after a certain time period, as after a number of minutes, hours, days, weeks, etc. In combination to that or as an alternative, the template update may be initiated by the physician, for example during a follow up session.

According to an embodiment of the invention, the biventricular (BiV) implantable cardiac stimulator contains a stimulation control unit, one or more stimulation units, an impedance measurement unit and an impedance evaluation unit. The stimulation control unit is operatively connected to one or more stimulation units to control delivery of stimulation pulses by the one or more stimulation units. The stimulation control unit is configured to assess ventricular contractility based on an impedance signal generated by the impedance evaluation unit and to switch between at least a univentricular left ventricular stimulation mode and a biventricular stimulation mode and to evaluate the ventricular contractility in relation to the respective ventricular stimulation mode.

The invention provides a strategy for leveraging CLS contractility measurements to both assess ventricular actuation responses and offer a means for adaptively configuring ventricular pacing to improve upon a blunted force-frequency relation common during univentricular pacing in patients with heart failure and conduction delay. The invention provides means for generating statistics to report the efficiency of implant/heart behavioral interactions and offers new algorithmic support for transitioning from LV-only pacing (used in cases where right-side conduction is largely intact) to biventricular (BiV) pacing based upon a measured reduction in the intended growth of patient-specific contractility, a behavior that emerges as pacing rates increase. Such adaptation can support improved device/patient coordination thus dynamically servicing key therapeutic needs in accordance with prevailing non-ambulatory conditions.

The invention includes the insight that a clinician selection of optimized CRM device parameter settings is typically informed by follow-up testing, statistics/home monitoring service center (HMSC) feedback, and direct in-clinic examinations. Such evaluations therefore only provide a snapshot of patient behavior with the potential to weight such surveys toward non-ambulatory response dynamics. When paired with available ventricular pacing configurations in biventricular (BiV) modes needed for CRT therapies, the clinician is typically only able to select either a univentricular left ventricular (LV-only) setting or a biventricular (BiV) setting where the pacing in one ventricle proceeds or aligns with that occurring in the other. Unfortunately, the clinician-selected ventricular pacing configuration then prevails between follow-ups without any means for adapting to changing patient needs emergent from higher frequency pacing. In a recent study [Vollmann et al. "Biventricular Pacing Improves the Blunted Force-Frequency", Circulation, 21. February 2006], it was demonstrated that higher rate pacing in patients with heart failure and conduction delay preferentially benefit from elevated contractility at higher rates in non-LV-only BiV modes as compared to LV-only BiV support.

The inventors also considered an adaptive CRT (aCRT) algorithm [Krum et al. "A novel algorithm for individualized cardiac resynchronization therapy: Rationale and Design of theAdaptive Cardiac Resynchronization Therapy Trial", American Heart Journal, Volume 163, Number 5] that provides a method for modulating ventricular pacing configurations in response to patient needs. The inventors found that instead of grading the efficacy of contractility (in addition to its monitoring of right-side conducted activity) the aCRT algorithm simply administers non-LV only BiV pacing above a set rate limit.

According to the present invention the contractility of a patient's ventricles is continuously monitored to provide a means for assessing the effectiveness of a selected fixed BiV pacing configuration, i.e. LV-only pacing or BiV pacing.

Further, in a preferred embodiment, the implant's monitoring of the ventricular contractility/response is used to alter the ventricular pacing configuration to maintain the highest dP/dt (contractility) condition. While this second facet of the invention could be established using a fixed rate threshold, by instead monitoring patient contractility the transitions between ventricular support modes could be adaptable to each individual and their prevailing physiologic needs.

In a preferred embodiment, the contractility determination unit contains or is connected to an impedance measurement unit and an impedance evaluation unit that is configured to process an impedance signal received from the impedance measurement unit and to generate an evaluated impedance signal that reflects myocardial contractility and wherein the stimulation control unit is configured to assess ventricular contractility based on the evaluated impedance signal and a respective stimulation mode. The impedance measurement unit preferably is connected to electrodes that are configured to allow an impedance measurement wherein impedance signal reflects blood volume in a ventricle.

In the context of the present invention, functionality of CLS is understood as adjusting a physiologically adequate stimulation rate for an implantable cardiac stimulator according to cardiac contractility in a continuous, self-regulating manner. In one preferred embodiment of the present invention, the cardiac contractility is determined according to impedance measurements. The impedance signal may be retrieved via a cardiac sensing and/or stimulation electrode which is fixated or at least is coupled to a ventricle or an atrium of the heart.

The measurements are performed between at least two electrode poles, wherein a first electrode pole may be formed by a tip electrode of an electrode lead and a second electrode pole may be formed by the can of the implantable cardiac stimulator. Alternatively, the at least two electrode poles may be formed by different electrodes of an electrode lead having multiple electrodes for sensing and/or pacing. The impedance signal is preferably measured in a continuous manner during consecutive heart cycles. The changes of the impedance signal that may be acquired with the configuration originate from the changing myocardial wall motion during the heart cycle. Considering the area around the at least one of the at least two electrode poles, there is an interface between blood and myocardium that varies during the heart cycle. The electric impedance of the myocardium is higher than the impedance of blood. In other words, when the heart is in a relaxed state, said interface of the electrode pole will contain a comparatively low portion of myocardium and a high portion of blood, wherein the measured impedance will be low, and vice versa when the heart is in a contracted state.

Preferably, for CLS, the intracardiac impedance curve after start of the ventricle contraction is measured. This measurement is carried out both for intrinsic and for stimulated events.

Further, the stimulation control unit preferably is configured to generate data for a data structure that contains contractility signal values in association with stimulation mode identifier values that identify the respective stimulation mode that prevailed when a respective contractility signal value was determined.

Preferably, the contractility signal reflects dP/dt in a right and/or left ventricle. The contractility determination unit can be a closed-loop-stimulation sensor or a closed-loop-stimulation sensor system.

In the context of the present invention, it is understood that a CLS sensor contains every type of sensor or sensor system which is suitable for performing CLS measurements in the manner described within the scope of the present invention. For instance, the CLS sensor can be an electrical, a mechanical, electromechanical or optical sensor, as e.g. an impedance sensor, a pressure sensor, an acceleration sensor, an acoustic sensor, an optical sensor or a combination of the said sensors. Moreover, the CLS sensor may include components and means for collecting, evaluating, processing, analysis and interpretation of the sensed signals. For example, the CLS sensor or sensor system may include units for performing mathematical operations of the acquired signals, e.g. calculation of sums and differences, averaging, calculation of weighting factors, calculating correlation factors, calculating time derivatives d/dt and the like. Preferably, the CLS sensor or sensor system may include units for interpreting detected and/or processed signals in order to associate said signals in the context of cardiac contractility as described within the scope of the present invention.

Preferably, the impedance measurement unit and an impedance evaluation unit that are configured to determine a plurality of impedance values between different pairs of electrodes connected or connectable to the impedance measurement unit and wherein the impedance evaluation unit is configured to generate left ventricular and right ventricular impedance signals reflecting left ventricular and right ventricular impedance values, respectively. It is even further preferred if the impedance evaluation unit is configured to generate evaluated left ventricular and right ventricular impedance signals that reflect left ventricular and right ventricular myocardial contractilities and wherein the stimulation control unit is configured to assess left and/or right ventricular contractility based on the evaluated impedance signal and a respective stimulation mode In order to provide automatic switching into the most suitable stimulation mode, it is preferred, if the stimulation control unit is configured to switch between a univentricular left ventricular stimulation mode and a biventricular stimulation mode depending on right and/or left ventricular contractility.

In order to allow a physician to determine suitable stimulation modes, it is preferred, if the biventricular implantable cardiac stimulator comprises a memory for storing contractility signal values in association with stimulation mode identifier values that identify the respective stimulation mode that prevailed when a respective contractility signal value was determined and a telemetry unit that is configured to enable an access to values in the memory by means of an external device.

According to this invention it is proposed to use the contractility measurements made available through the CLS feature to assess ventricular pumping efficacy. At a minimum this assessment of ventricular contractility is used to present new (or a set of new) clinician-viewable statistics that can further benchmark the device/patient interactions (especially in the context of CRT patient therapies).

It has been observed that CRT therapies that administer pacing in a univentricular fashion (i.e. LV-only pacing configurations) fail to optimally support the maximization of the LV dP/dt output responses in response to patient rate adaptation. At higher pacing rates, ventricular contractility is more efficient when pacing occurs in both the right ventricle and the left ventricle. For CRT patients with variable between follow-up metabolic demand, the pacing configurations that appeared optimal during the non-ambulatory settings of a typical clinical visit may, in turn, prove suboptimal in the day-to-day activities of various patients. With new statistics in hand that report measured ventricular contractility as a function of rate, e.g. in the form of a histogram, the clinician is given a new metric (or set of metrics) for evaluating the performance of BiV pacing support. In cases of CRT non-responders this information could serve to highlight potential avenues for improved support.

In a further improved embodiment the functionality of this assessment of ventricular contractility, the implant can leverage the measured values to adapt the pacing configuration. Such an effect typically emerges in cases where the clinician prefers to employ LV-only ventricular support whenever right-side heart conduction exists. At elevated rates, the ventricular support can then be transitioned to a BiV pacing support mode that better insures a maximized left ventricular contractile response. Instead of using the surrogate cue of a rate limit for this transition, the implant can instead elect to switch from LV-only pacing support to BiV support in response to the direct metric of contractility.

As the force-frequency relationship of individual patients can vary, enabling adaptable ventricular pacing on the basis of individualized contractility measurements is a better choice for administering patient-specific care. In an even further improved embodiment, the transition can occur in response to an LV-only vs. non-LV-only contractility comparison algorithm. The implantable medical device can initiate periodic searches for improved contractility subject to BiV pacing. If measurements of contractility showed higher values during the search performed by the periodic switch to BiV conditions, the implantable medical device can elect to perform ongoing pacing through a full transition to the non-LV-only pacing mode.

With enough resolution, CLS-enabled contractility measurements can ultimately service dynamic tuning of interventricular (VV) delays by evaluating both right ventricular and left ventricular dynamics throughout the cardiac cycle. The preferred method seeks the peak contractility within each ventricle and align the timing of such peaks by varying the offset of BiV paced events. Such tuning can be used to ensure the best coordinated right ventricular and left ventricular contraction behaviors and maintain a septal wall orientation better aligned with healthy physiologically dynamics. This type of tuning would necessarily demand a periodic survey of right ventricular and left ventricular contractilities paired with an interventricular (VV) delay search algorithm that intentionally varies the relative timing of each ventricular stimulation pulse and selects the VV delay that maximizes dP/dt conditions.

Other features which are considered as characteristic for the invention are set forth in the appended claims.

Although the invention is illustrated and described herein as embodied in a bi-ventricular implantable medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 5A) and for biventricular stimulation mode (biventricular pacing; FIG. 5B);

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
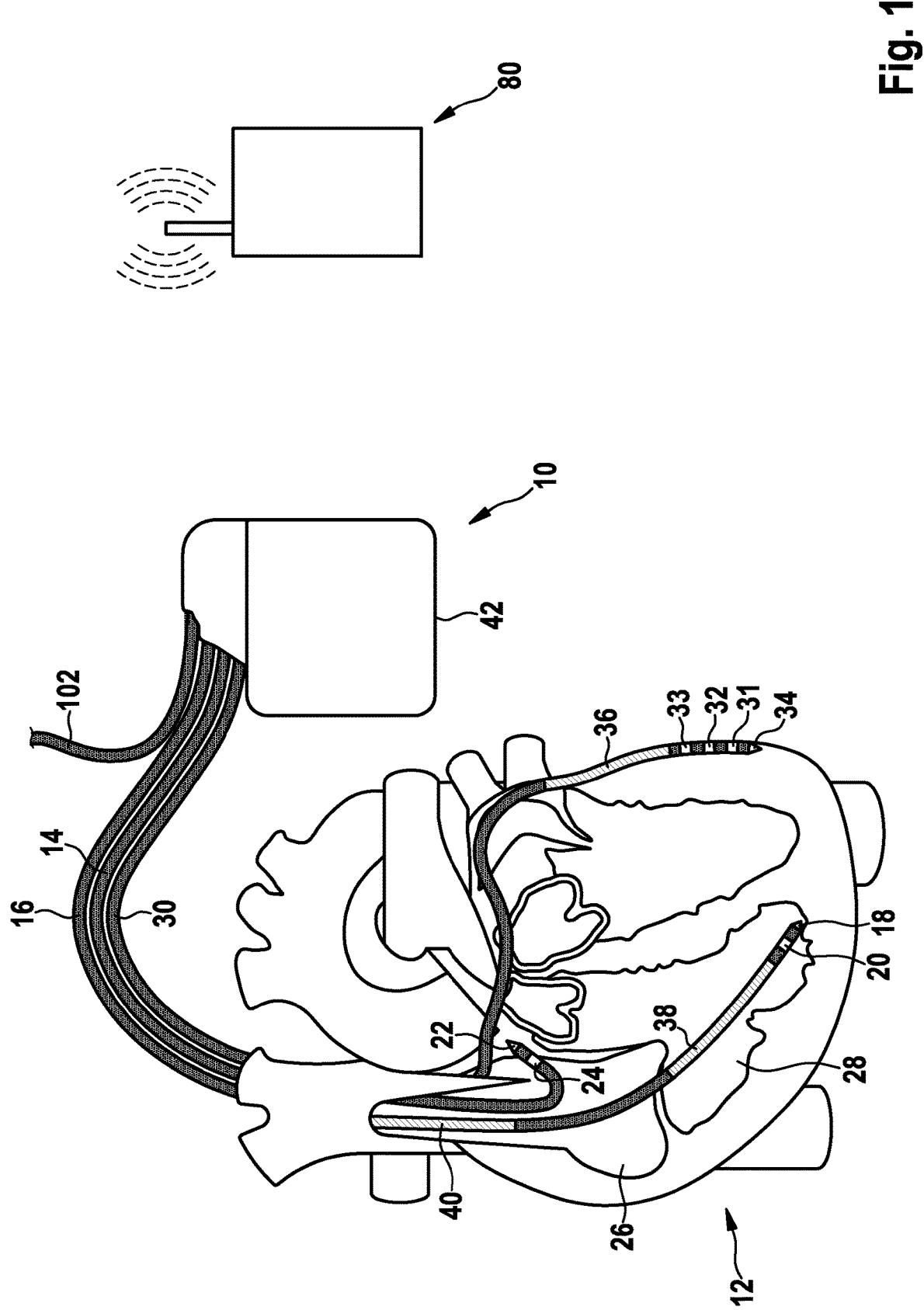
FIG. 1 is an illustration of a three chamber biventricular implantable cardioverter/defibrillator (ICD)

In FIG. 1 the implantable medical device (also referred to as implantable cardiac device) is a three chamber biventricular pacemaker and cardioverter/defibrillator 10 that is connected to pacing/sensing leads placed in a heart 12 is illustrated.

As shown in FIG. 1, the preferred embodiment is to couple the disclosed technology with an implantable biventricular defibrillator.

The implantable medical device 10 is electrically coupled to heart 12 by way of leads 14, 16 and 30.

Lead 14 is a right atrial electrode lead that has a pair of right atrial electrodes 22 and 24 that are in contact with the right atria 26 of the heart 12.

Lead 16 is a right ventricular electrode lead that has a pair of ventricular stimulation and sensing electrodes 18 and 20 that are in contact with the right ventricle 28 of the heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Figure 2:
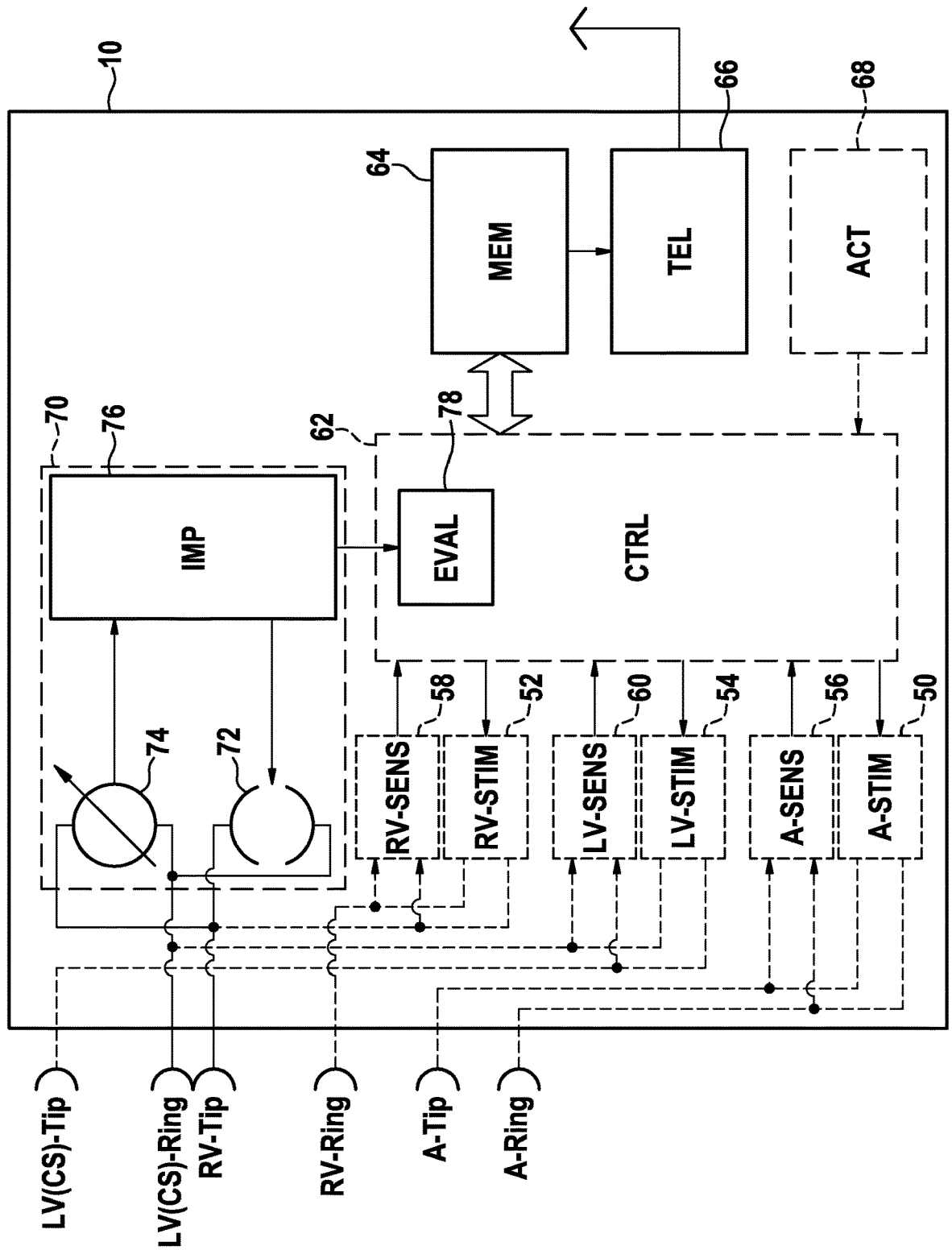
FIGS. 2 and 3 are schematic diagrams of two alternative embodiments of device modules of the ICD of FIG. 1.
Figure 3:
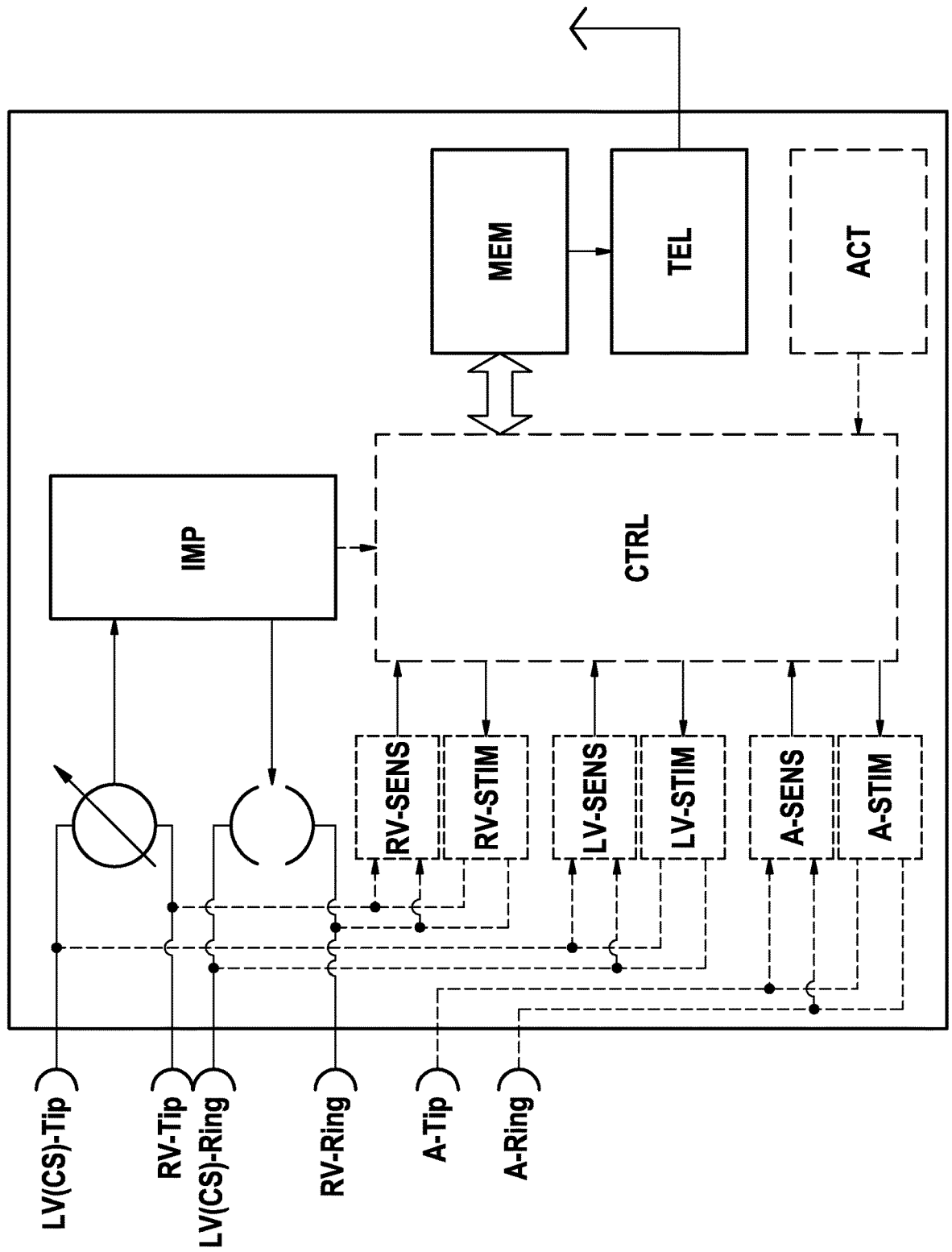

Lead 30 is a left ventricular electrode lead passing through the coronary sinus of heart 12 and having left ventricular ring electrodes LV RING 31, 32 and 33 and a left ventricular tip electrode LV TIP 34. Further, a left ventricular defibrillation shock coil 36 is arranged on lead 30. It is noted that the number of left ventricular ring electrodes may vary depending on the electrode lead that is used. In the context of FIGS. 2 and 3, one left ventricular ring electrode LV-RING is referred to the acts as pars pro toto.

Implantable medical device 10 has a case 42 made from electrically conductive material such as titanium that can serve as a large surface electrode IMD CASE.

The plurality of electrodes 18, 20, 22, 24, 31, 32, 33, 34, 36, 38 and 40 connected to implantable medical device 10 together with case 42 allow for a number of different electrode configurations for measuring intrathoracic and intracardiac impedance.

The parameters from which cardiac contractility can be derived may be measured via different measurement vectors. For example, the measurements may be performed in a bipolar manner, i.e. between a tip electrode and a ring electrode of one of the electrode leads 14, 16, 30; or in an unipolar manner between a tip electrode or another electrode of one of the electrode leads 14, 16, 30 and the case 42 of the implantable medical device 10. Moreover, in order to perform such measurements, it is also possible to inject a forcing function from a right ventricular electrode to a left ventricular electrode (for instance between a ring electrode and a ring electrode, a tip electrode and a tip electrode, or between a tip electrode and a ring electrode or vice versa) and measuring a response function between the same electrodes or via another pair of electrodes. Further possible measurement vectors (resulting from different measurement electrode combinations) are illustrated with respect to FIG. 11. In one example, the parameters which are measured in the way described are intracardiac impedance values.

Referring to FIG. 2 illustrating a simplified block diagram of an implantable medical device 10. During operation of the pacemaker leads 14, 16 and 30 are connected to respective output/input terminals of pacemaker 10 as indicated in FIG. 2 and carry stimulating pulses to the tip electrodes 18, 22 and 34 from a right atrial stimulation pulse generator A-STIM 50, a right ventricular pulse generator RV-STIM 52 and a left ventricular pulse generator LV-STIM 54, respectively. Further, electrical signals from the right atrium are carried from the electrode pair 22 and 24, through the lead 14, to the input terminal of a right atrial channel sensing stage A-SENS 56; and electrical signals from the right ventricle are carried from the electrode pair 18 and 20, through the lead 16, to the input terminal of a right ventricular sensing stage RV-SENS 58. Likewise electrical signals from the left ventricle are carried from the electrode pair 32 and 34, through the lead 30, to the input terminal of a left ventricular sensing stage LV-SENS 60.

Controlling the implantable medical device 10 is a control unit CTRL 62 that is connected to sensing stages A-SENS 56, RV-SENS 58 and LV-SENS 60 and to stimulation pulse generators A-STIM 50, RV-STIM 52 and LV-STIM 54. Control unit CTRL 62 receives the output signals from the atrial sensing stage A-SENS 56, from the right ventricular sensing stage RV-SENS 58 and from the left ventricular sensing stage LV-SENS 60. The output signals of sensing stages A-SENS 56, RV-SENS 58 and LV-SENS 60 are generated each time that a P-wave representing an intrinsic atrial event or an R-wave representing an intrinsic ventricular event, respectively, is sensed within the heart 12. An As-signal is generated, when the atrial sensing stage A-SENS 56 detects a P-wave and a RVs-signal is generated, when the right ventricular sensing stage RV-SENS 58 detects an R-wave.

These sense events are used by control unit CTRL 62 as fiducial points of the respective intracardiac electrograms picked up by the sensing stages A-SENS 56, RV-SENS 58 and LV-SENS 60, respectively.

Control unit CTRL 62 also generates trigger signals that are sent to the atrial stimulation pulse generator A-STIM 50, the right ventricular stimulation pulse generator RV-STIM 52 and the left ventricular stimulation pulse generator LV-STIM 54, respectively. These trigger signals are generated each time that a stimulation pulse is to be generated by the respective pulse generator A-STIM 50, RV-STIM 52 or LV-STIM 54. The atrial trigger signal is referred to simply as the "A-pulse", and the ventricular trigger signal is referred to as the "RV-pulse" or the "LV-pulse", respectively. During the time that either an atrial stimulation pulse or ventricular stimulation pulse is being delivered to the heart, the corresponding sensing stage, A-SENS 56, RV-SENS 58 and/or LV-SENS 60, is typically disabled by way of a blanking signal presented to these amplifiers from the control unit CTRL 62, respectively. This blanking action prevents the sensing stages A-SENS 56, RV-SENS 58 and LV-SENS 60 from becoming saturated from the relatively large stimulation pulses that are present at their input terminals during this time. This blanking action also helps prevent residual electrical signals present in the muscle tissue as a result of a stimulation pulse delivered from pacemaker 10 from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 62 contains circuitry for timing ventricular and/or atrial stimulation pulses according to an adequate stimulation rate that can be adapted to a patient's hemodynamic need as pointed out below.

Still referring to FIG. 2, the implantable medical device 10 includes a memory circuit MEM 64 that is coupled to the control unit CTRL 62 over a suitable data/address bus ADR. This memory circuit MEM 64 allows certain control parameters, used by the control unit CTRL 62 in controlling the operation of the implantable medical device 10, to be programmably stored and modified, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 64 for later retrieval and analysis.

A telemetry circuit TEL 66 is further included in the implantable medical device 10. This telemetry circuit TEL 66 is connected to the control unit CTRL 62 by way of a suitable command/data bus. Telemetry circuit TEL 66 allows for wireless data exchange between the implantable medical device 10 and some remote programming or analyzing device which can be part of a centralized service center serving multiple pacemakers.

The implantable medical device 10 in FIG. 2 is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE 56, the atrial stimulation pulse generator A-STIM 50 and corresponding portions of the control unit CTRL 62, may be referred to as the atrial channel. Similarly, those portions of the pacemaker 10 that interface with the right ventricle 28, e.g., the lead 16, the R-wave sensing stage RV-SENSE 58, the ventricular stimulation pulse generator RV-STIM 52, and corresponding portions of the control unit CTRL 62, may be referred to as the ventricular channel.

In order to be able to detect periods of physical activity of a patient indicating that the patient is awake and in order to allow rate adaptive pacing, the pacemaker 10 further includes a physiological sensor ACT 68 that is connected to the control unit CTRL 62 of the pacemaker 10. While this sensor ACT 68 is illustrated in FIG. 2 as being included within the pacemaker 10, it is to be understood that the sensor may also be external to the implantable medical device 10, yet still be implanted within or carried by the patient. A common type of sensor is an accelerometer, such as a piezoelectric crystal, mounted to the case of the pacemaker. Other types of physiologic sensors are also known, such as sensors that sense the oxygen content of blood, respiration rate, blood pH, intracardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient. The output of sensor 68 represents an activity level.

By means of the output signal of activity sensor 68 the control unit 62 is able to assign each intrinsic heart rate to an activity thus enabling collection of intrinsic heart rate value for a patient's state of rest and a patient's state of exercise separately.

The control unit CTRL 62 is adapted to determine an adequate heart rate or stimulation rate in any manner known as such, including closed loop stimulation (CLS).

Because the contractility of the heart can be controlled physiologically by the autonomic nervous system, the detection of the contractility can also be utilized to adjust a physiologically adequate stimulation rate in rate-adaptive cardiac pacemakers. This type of stimulation rate control, as addressed above, is also known as closed loop stimulation (CLS).

Contractility of the heart can be determined by measuring intracardiac impedance and evaluating the time course of the impedance signal and in particular the first derivative of the impedance signal.

For CLS, the intracardiac impedance response after the start of the ventricular contraction is measured. This measurement is carried out both for intrinsic and for stimulated events. There is a direct dependency between the right-ventricular impedance response and the contraction dynamics. The contraction dynamics, in turn, is a parameter for the stimulation of the heart by the sympathetic nervous system.

Closed loop stimulation is, as mentioned above, the control of the stimulation rate with a rate-adaptive cardiac pacemaker.

For impedance measurement, an impedance determination unit 70 is provided. Impedance determination unit 70 contains a constant current source 72 that is connected or can be connected to electrodes for intracorporal placement as shown in FIG. 1. In order to allow for a plurality of impedance measurement electrode configurations, preferably some means of switching is provided between the constant current source 72 and the electrode terminals of the implantable medical device 10. The switch is not shown in FIG. 2. Rather, particular impedance measurement configurations are shown as examples.

Similarly, a voltage measuring unit 74 for measuring a voltage corresponding to a current fed through a body by the constant current source is provided and can be connected to a number of electrodes although a switch for switching between these configurations is not shown in FIG. 2.

As an alternative to constant current source 72 a constant voltage source can be provided to generate the forcing function. Then, the measuring unit will be adapted to measure current strength of a current fed through a body by the constant voltage source.

Both, constant current source 72 and voltage measurement unit 74, are connected to an impedance value determination unit 76 that is adapted to determine an impedance value for each measuring current pulse delivered by the constant current source 72.

Further, an impedance evaluation unit 78 is provided either as a separate unit or as part of control unit CTRL 62 as depicted in FIG. 2. The evaluation unit 78 is connected to the impedance measurement unit 70 and is adapted to evaluate a sequence of consecutive impedance values determined by the impedance measurement unit. The evaluation unit 78 contains a signal generator module (not shown) to construct the intracardiac impedance or conductance signal reflecting the time course of the impedance measurement unit's output signal and its derivative.

The evaluation unit 78 further contains a filter module (not shown) to filter the intracardiac impedance signal.

The evaluation unit 78 is further connected to the right ventricular stimulation stage RV-STIM 52 and the right ventricular sensing stage RV-SENS 58 in order to receive signals representing cardiac events, namely right ventricular stimulation events RVp or right ventricular sense events RVs, respectively. Moreover, the evaluation unit can be connected to the right atrial stimulation stage A-STIM 50 and the right atrial sensing stage A-SENS 56 in order to receive signals representing cardiac events, namely right atrial stimulation events Ap or right atrial sense events As, respectively. The evaluation unit can as well be connected to the left ventricular stimulation stage LV-STIM 54 and the left ventricular sensing stage LV-SENS 60 in order to receive signals representing cardiac events, namely left ventricular stimulation events LVp or left ventricular sense events LVs, respectively.

The constant current source 72 has its two poles connected to different connectors for different electrodes as for example the right ventricular tip electrode and the left ventricular ring electrode (FIG. 2) or the left ventricular ring electrode and the right ventricular ring electrode (FIG. 3). The voltage measuring unit 74 has two poles connected to, for example, a connector for the left ventricular ring electrode and the right ventricular tip electrode (FIG. 2) or the left ventricular tip electrode and the right ventricular tip electrode (FIG. 3). However, depending on the type and pursued functionalities of the implantable medical device 10, other configurations for connecting the poles of current source 72 and voltage source 74 are also possible.

Impedance measurement is carried out by injecting a constant current and sampling the resulting voltage.

The measuring current is preferably pulsed. Typically, the measuring current will feature biphasic pulses wherein two constant current pulses of opposite polarity form one pulse package. Between two consecutive pulse packages a time gap is provided, which is significantly longer than the duration of one pulse package. The constant current pulses within one pulse package are each of the same intensity and of same duration. They only have different polarities. The typical value for the intensity of the constant current pulses is between 50 µA and 600 µA. The typical pulse duration of a single constant current pulse is about 15 µs.

The time gap between each two consecutive pulse packages may be 500 times longer than the duration of one constant current pulse. The two constant current pulses of opposite polarity within one pulse package may not follow immediately each other but may have a time gap there between. This time gap however, will be very short compared to the time gap between two consecutive pulse packages. Furthermore, consecutive pulse packages may present alternating global polarities such that a first pulse package, for example, begins with a positive constant current pulse whereas the following pulse package begins with a negative constant current pulse and ends with a positive constant current pulse.

Figure 4A:
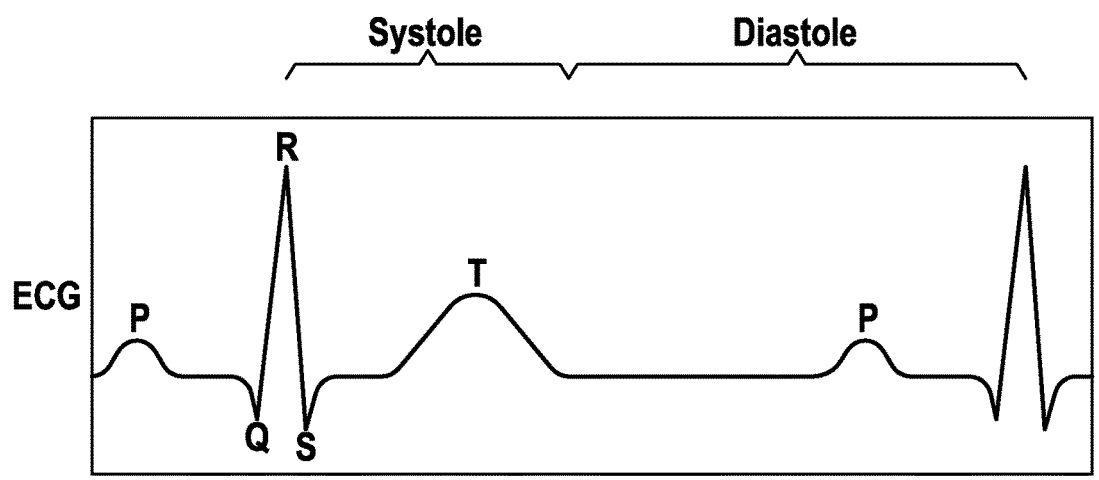
FIG. 4A is a graph of a typical electrocardiogram.
Figure 4B:
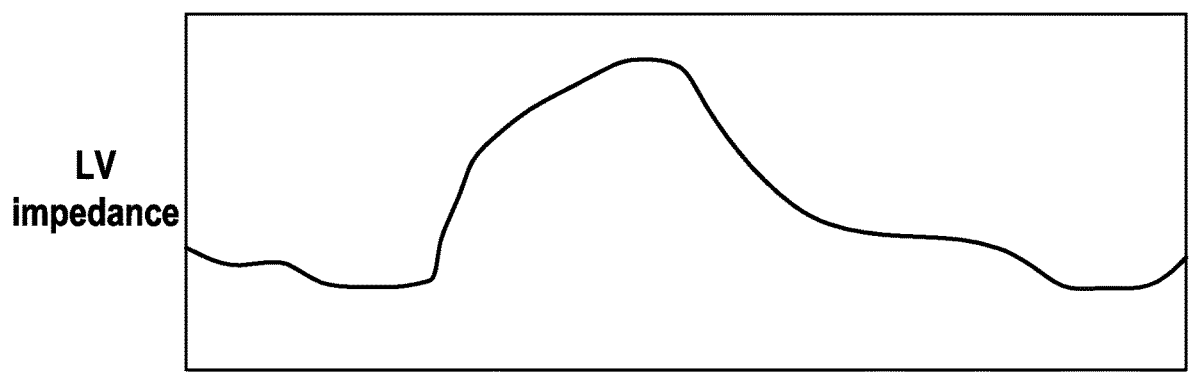
FIG. 4B is a graph depicting a typical time course of the left ventricular impedance Z.

In FIG. 4B a typical time course of the left ventricular impedance Z is depicted. FIG. 4A shows a typical electrocardiogram. When the left ventricle has its smallest volume at the end of the systole (contraction of the ventricle) the impedance Z has a maximum. The time course of the impedance inversely reflects the time course left ventricular volume.

The main purpose of the sensing stages 56, 58 and 60 is to detect a natural (intrinsic) contraction of the respective heart chamber in order to generate a sense event signal like an atrial sense event As, a right ventricular sense event RVs and a left ventricular sense event LVs. These sense events are processed by the control unit CTRL 62 in order to inhibit a delivery of a stimulation pulse when the pacemaker is operating in a demand mode or in order to determine a time interval between an atrial event and a point of time, when the course of the left ventricular intracardiac impedance reaches its minimum value, see below.

Another type of event to be processed by the control unit CTRL 62 would be the delivery of a stimulation pulse to a respective heart chamber. Delivery of a stimulation pulse causes a paced event such as an atrial paced event Ap, a right ventricular paced event RVp and a left ventricular paced event LVp.

Memory MEM 64 among other considerations serves for storing contractility signal values and stimulation mode identifier values that identify the respective stimulation mode that prevailed when a respective contractility signal value was determined in a coordinated manner.

The impedance evaluation unit EVAL 78 is adapted to determine from the time course of the impedance value time periods for each cardiac cycle that correspond to a filling period, an isovolumic contraction period, an ejection period and an isovolumic relaxation period, respectively.

When in use, the implantable cardiac device measures the intracardiac impedance (Z), from which parameters correlating to myocardial contractility can be derived; see inter alia Schaldach M, Hutten H. "Intracardiac Impedance to Determine Sympathetic Activity in Rate Responsive Pacing." PACE 1992; 15: 1772-86; Schaldach M, Urbaszek A, Stöbel J, Heublein B. "Rate-Adaptive Pacing Using a Closed-Loop, Autonomic Nervous System Controlled Pacemaker", JHK Coll Cardiol 1995; or M. Anelli-Monti, B. Anelli-Monti, H. Mächler, A. Wasler, W. Weihs, W. Klein, "CLOSED LOOP Stimulation—Ein neues Herzschrittmacher-Konzept zur Frequenzadaptation mittels eines Kontraktilitätssensors", J Kardiol 1999; 6: 21-5.

Further, a plurality of timing intervals can be derived that characterize different phases of the cardiac contraction, such as the isovolumic contraction time (IVCT), isovolumic relaxation time (IVRT), ejection time (ET), and filling time (FT). The total isovolumic time (TIVT) is the sum of IVCT and IVRT, and the cardiac cycle length (CL) is the sum of IVCT, IVRT, ET, and FT.

Figure 5A:
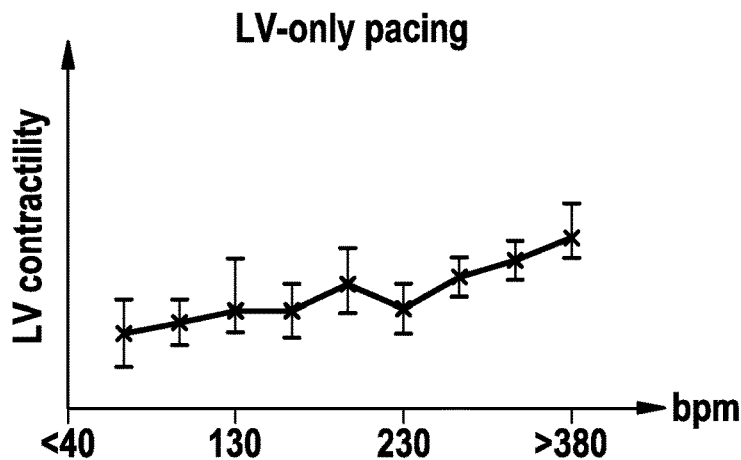
FIGS. 5A and 5B are graphs showing exemplary contractility plots for a left ventricular stimulation mode (left ventricular pacing.
Figure 5B:
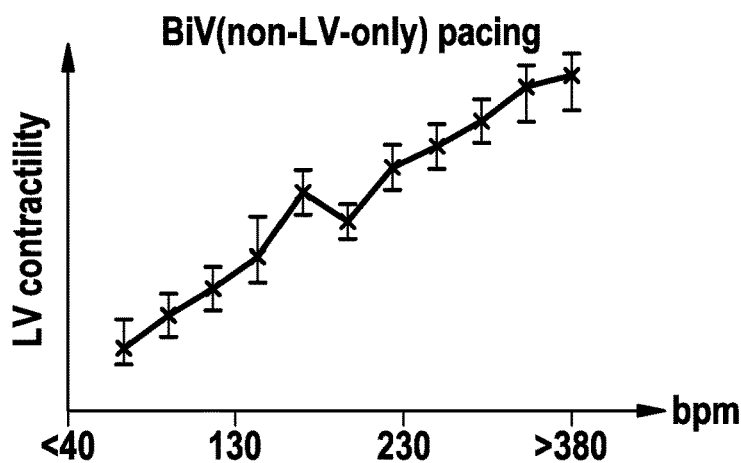

The concept of the invention is illustrated by way of example in FIGS. 5A and 5B, which show plots for exemplary left ventricular contractility according to the heart rate in beats per minute (bpm). FIG. 5A shows left ventricular contractility for left ventricular stimulation mode only, wherein FIG. 5A shows left ventricular activity for biventricular stimulation mode. It can be observed that with increasing heart rate cardiac, LV contractility can be significantly improved by applying biventricular stimulation instead of LV-only pacing.

Figure 6:
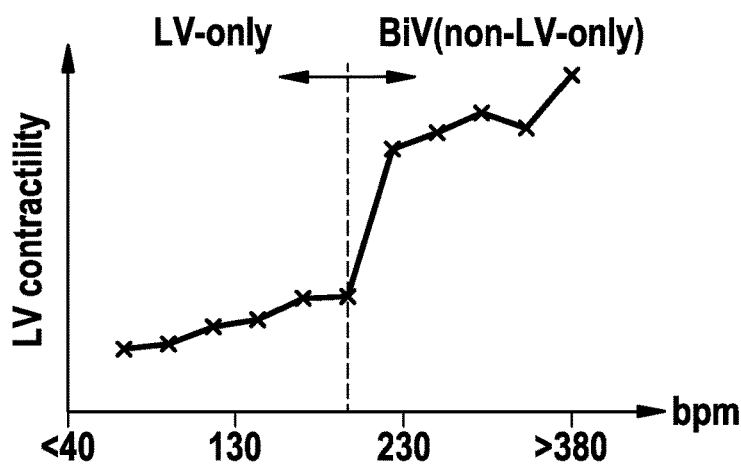
FIG. 6 is a graph showing an exemplary contractility plot illustrating a device enabled transition between a left-ventricular stimulation mode and a biventricular stimulation mode and vice versa.

FIG. 6 shows a plot of the LV contractility according to the heart rate in case the implantable medical device would be configured according to the present invention. In this case, the implantable medical device operates in the LV-only pacing mode when the physiological demand is low. When the physiological demand increases and reaches a certain limit, which is detected by the implantable medical device according to a parameter indicating cardiac contractility, the implantable medical device automatically switches to biventricular stimulation mode, which is illustrated in FIG. 6 by the dotted vertical line and the leap in the course of LV contractility.

According to the invention, the stimulation control unit 62 can be configured to switch to a biventricular stimulation mode when the implantable medical device 10 is in a LV-only stimulation mode and the stimulation control unit 62 determines that the contractility was suboptimal.

The stimulation control unit 62 can be configured to initiate a transition between the stimulation modes in the course of a periodic search where the implantable medical device 10 checks LV-only contractility versus Non LV-only biventricular contractility and above a certain limit elects to alter the ventricular stimulation mode to be applied further on.

Such a periodic search can be enabled above certain rates or it can persistently run (regardless of rate) and when the contractility difference between LV-only and non-LV-only settings exceeded one specified threshold the transition to BiV (non-LV-only) pacing can be enabled; see FIG. 6.

Preferably, the stimulation control unit 62 is configured to determine an optimum stimulation mode depending on myocardial contractility automatically. This can be achieved if the stimulation control unit is configured to apply the method as follows:

Initially the implantable medical device is either in the left ventricular stimulation mode or in the biventricular stimulation mode.

In either case, the stimulation control unit 62 measures cardiac contractility and determines whether the cardiac contractility is within a certain range and/or below/above a certain threshold value within a certain search window. The threshold value may be adapted according to the values within the search window, e.g. according to an average value.

If cardiac contractility is comparatively low within the search window, e.g. below a certain threshold value, the stimulation control unit 62 will maintain the left ventricular stimulation mode or will switch into the left ventricular stimulation mode, depending on whether the previous mode was a left ventricular stimulation mode or a biventricular stimulation mode.

If the stimulation control unit 62 determines that the cardiac contractility within the search window is above the threshold value, the left ventricular stimulation mode or will be switched into the biventricular stimulation mode or will maintain the biventricular stimulation mode, again depending on whether the previous mode was a left ventricular stimulation mode or a biventricular stimulation mode.

In this context, evaluations of the cardiac contractility may be performed on a beat-by-beat basis. The beat-by-beat measurements may be compared adapted according to templates that are periodically acquired in either follow-up or ambulatory states. Such templates can be determined according to the measured contractility response depending on the heart rate. Moreover, different templates should be generated for LV-only pacing and biventricular pacing, wherein the templates may be updated periodically, for instance based on a predetermined number of hours. Such templates may be plots similar to those shown in FIG. 5A and FIG. 5B. As a next step, a difference plot may be calculated between the LV-only pacing response and biventricular pacing response values, wherein a threshold difference is set in a point where the contractility difference becomes appropriately high. The corresponding contractility value in the LV-only pacing response plot can then be set as threshold value, i.e. the implantable medical device is configured to measure and evaluate the prevailing cardiac contractility on a beat-by-beat basis switches from LV-only pacing mode into biventricular pacing mode as soon as said threshold value has been crossed.

Thereafter, the stimulation control unit 62 performs a search to compare contractility in the biventricular stimulation mode (herein also called "biventricular contractility") with contractility in the left ventricular stimulation mode (herein also called "left ventricular contractility"). Stimulation control unit 62 then determines whether or not the biventricular contractility is sufficiently (e.g. by a predetermined margin) greater than the left ventricular contractility. If that is not the case, the left ventricular stimulation mode is maintained or enabled, respectively. In case the biventricular contractility is sufficiently greater than the left ventricular contractility, stimulation control unit 62 maintains or enable the biventricular stimulation mode.

It is noted that this procedure can be performed independent from a rate check, that is, the determination whether or not the stimulation rate is above a search window rate limit and the switching into the left ventricular stimulation mode depending on the result of this check can be omitted.

Figure 7A:
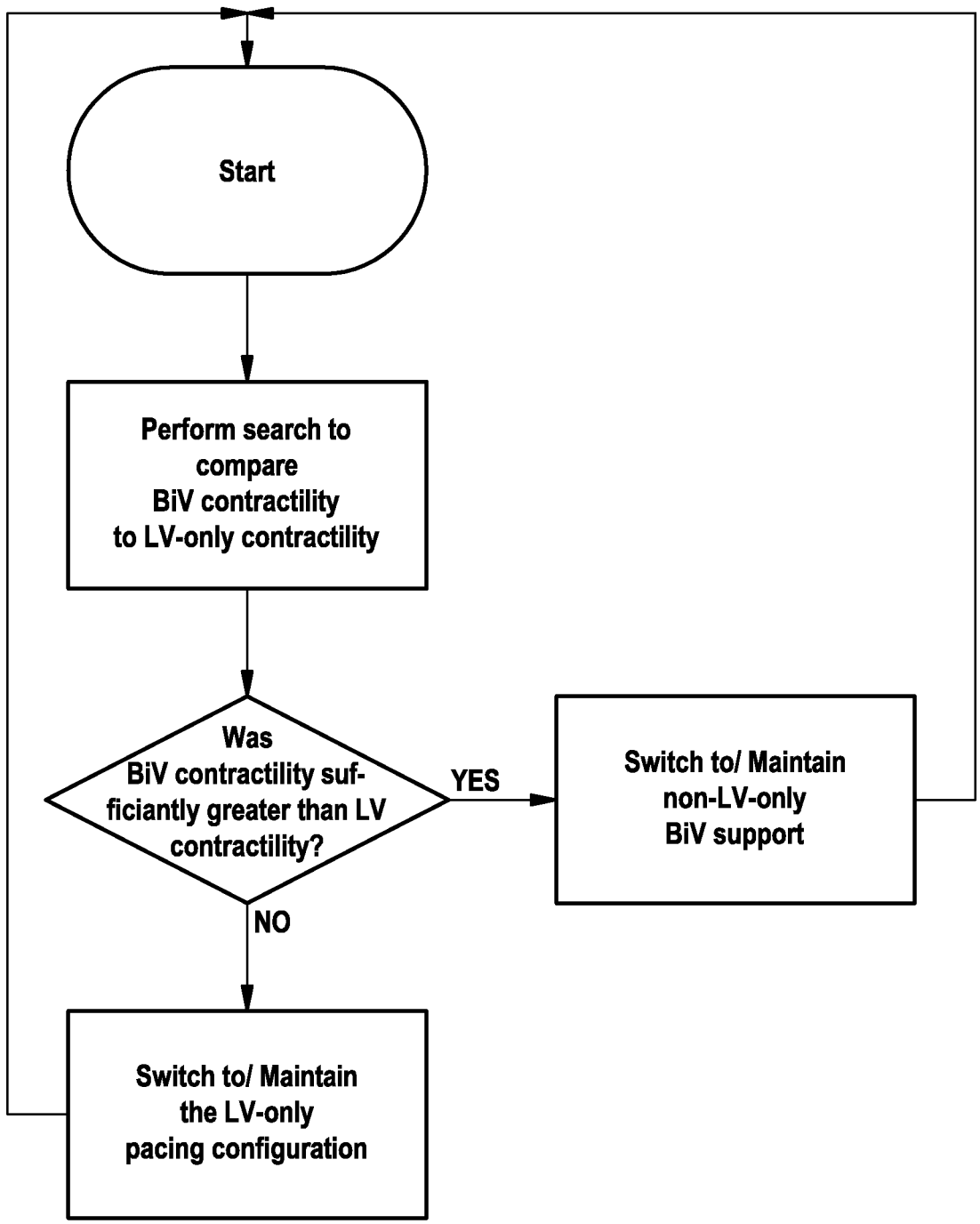
FIG. 7A is a flow chart illustrating an exemplary flow diagram of one possible contractility search algorithm.

FIG. 7A shows an exemplary flow diagram of one possible contractility search algorithm. At 'Start', the implantable medical device performs cardiac contractility measurements on a beat-to-beat basis. Alternatively, cardiac contractility measurement data could have been recorded beforehand which are used by the implantable medical device for performing the contractility search algorithm. In the step 'Perform search to compare BiV contractility to LV-only contractility', the implantable medical device e.g. compares the acquired contractility data with the determined templates and/or computes updated templates as described previously. According to the comparison, the implantable medical device either switches the mode from LV-only pacing to biventricular pacing or vice versa, or maintains the preconfigured mode.

Figure 7B:
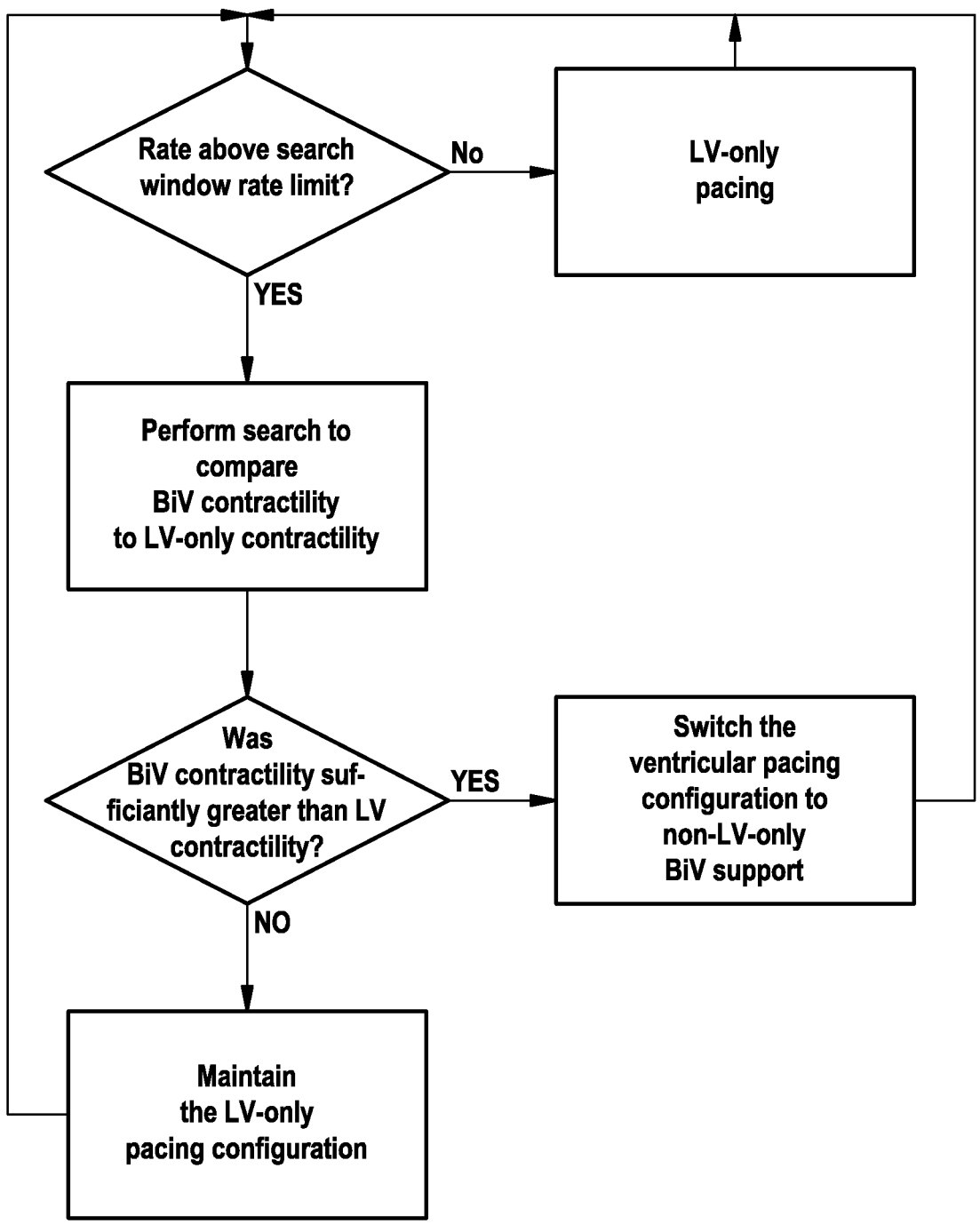
FIG. 7B is a flow chart illustrating an exemplary flow diagram of one possible rate-triggered contractility search algorithm.

FIG. 7B is an exemplary flow diagram of one possible embodiment of the contractility search algorithm involving the step 'Rate above search window rate limit?' bringing evaluation of the heart rate into the algorithm.

In possible embodiments, the proposed search algorithm may contain a combination of heart rate evaluation and the expiration of a timer to dictate the need for revised evaluations of CLS contractility templates. This can be for instance implemented by a query structure like: if 'X or more hours have expired' AND 'the patient rate is Y or above', a new cycle to update the contractility template is required.

In a possible embodiment of the present invention, the contractility templates can be determined depending on the heart rate for LV-only pacing and BiV pacing, wherein the templates can e.g. be established through a follow-up session.

If contractility measurements were recorded and/or assessed by the implant for both ventricles (see FIG. 8) then, when paired with periodic modulations of VV delay settings, the implant could furthermore tune and optimize VV delays between follow-ups.

Figure 8:
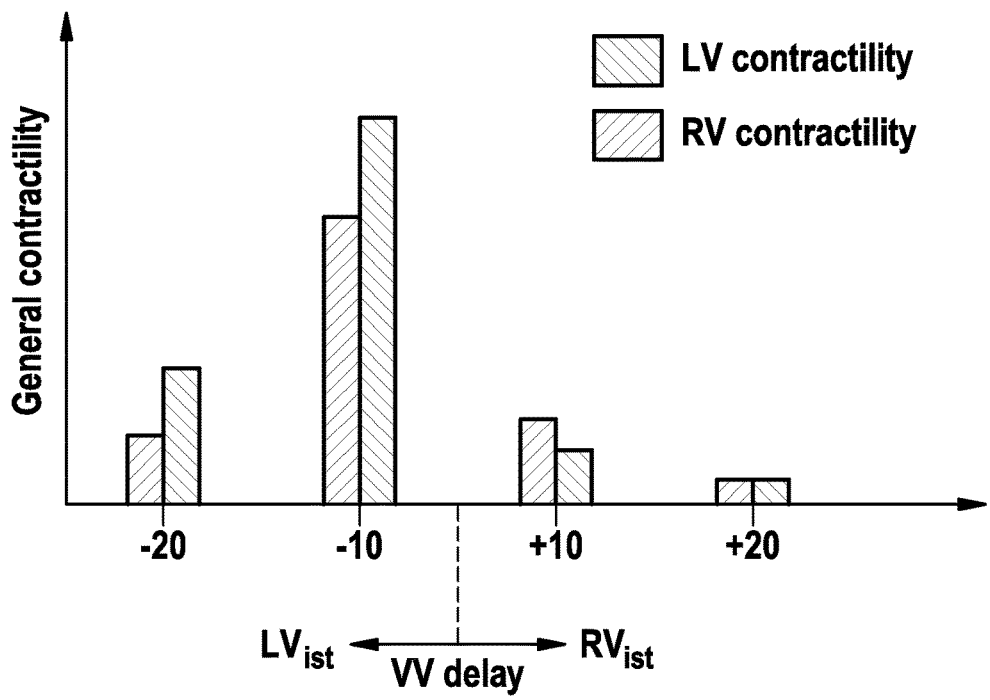
FIG. 8 is a graph illustrating exemplary statistics reflecting a data structure generated by the stimulation control unit 62 and stored in memory 64.

The graphic in FIG. 8 illustrates exemplary statistics reflecting a data structure generated by the stimulation control unit 62 and stored in memory 64 that can be used for VV timing optimization, internal to the implant.

Ideally, stimulation parameters are chosen so that a simultaneous (coordinated) contraction of the right ventricle and the left ventricle occurs.

Figures 9A, 9B, 9C:
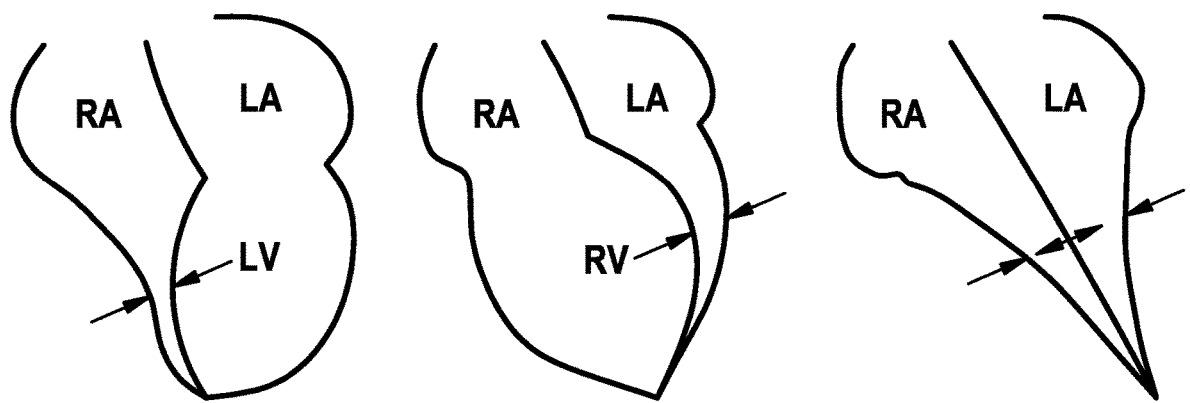
FIGS. 9A to 9C are illustrations showing the effect of bad or good ventricular coordination, respectively.

FIGS. 9A to 9c illustrate the effect of bad or good ventricular coordination, respectively. FIGS. 9A and 9B illustrate cases where the right ventricular and the left ventricular con-tractions are not well coordinated and thus the septal wall moves away from the central plane in the non-physiologic fashion. In the example illustrated FIG. 9A the left ventricular contraction occurs too early with respect to the right ventricular contraction while in the example depicted in FIG. 9B the right ventricular contraction occurs too early with respect to the left ventricular contraction.

Ideally, the right ventricular and the left ventricular conductions are well coordinated so that their septal maintains the fixed, centred position; see FIG. 9C.

The intracardiac impedance (Z) can be measured in various means. Preferably, the impedance vectors span across the left ventricle (LV) to reflect (at least) the volume change of the left ventricle.

Figure 10B:
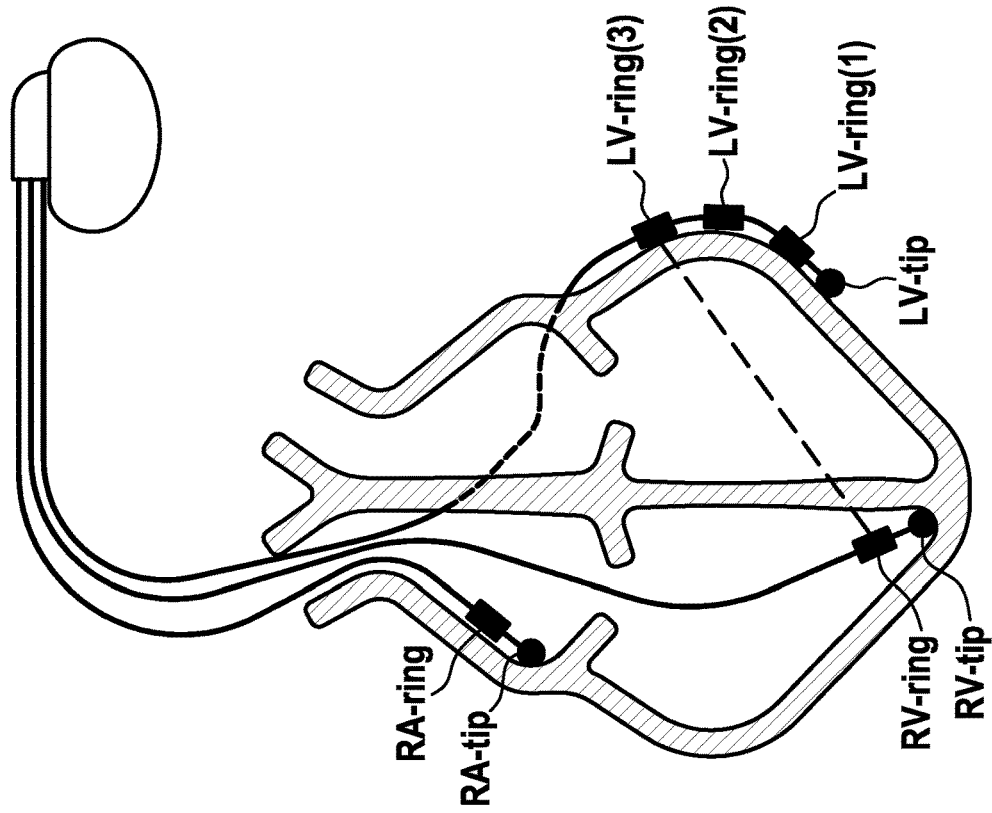
FIGS. 10A and 10B are illustrations showing two electrode configurations that allow impedance measurement.
Figure 10A:
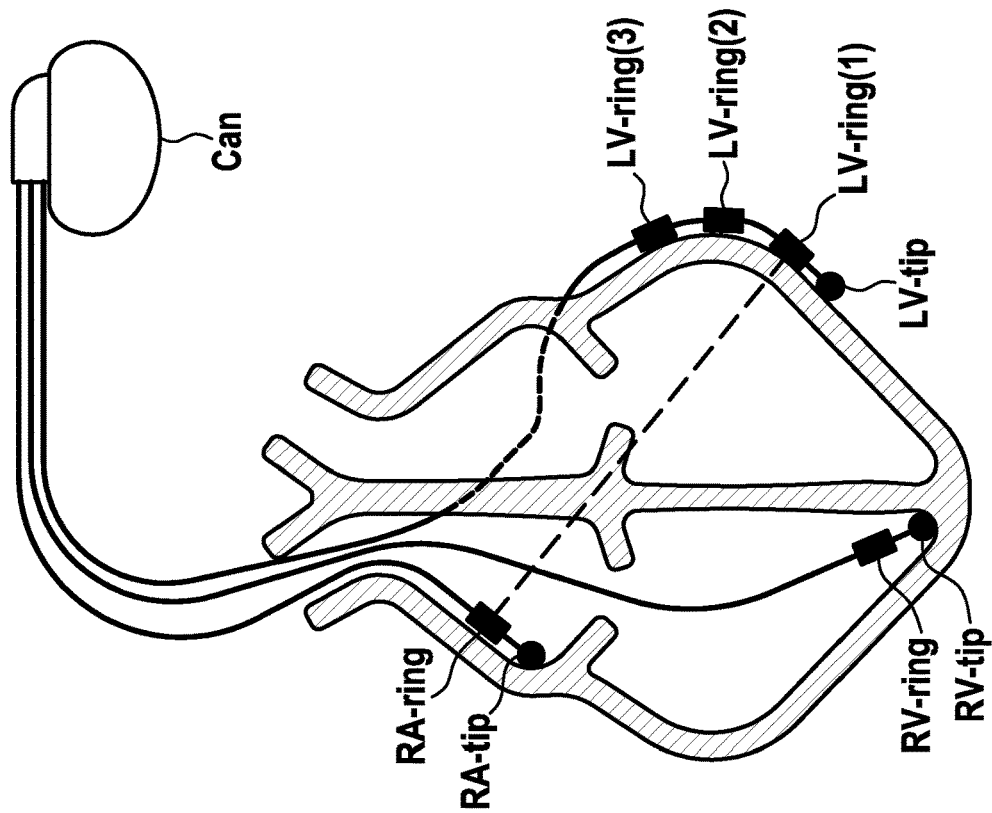

FIGS. 10A and 10B show two typical examples. In FIG. 10A, subthreshold (that is, non-stimulating) biphasic current pulses are injected between the RA tip and LV tip electrodes, and the voltage is measured between the RA ring and LV ring electrodes. The ratio of the measured voltage to the injected current then approximately represents the impedance between the distal end of the RA lead and the distal end of the LV lead. In FIG. 10B, subthreshold biphasic current pulses are injected between the RV tip and LV tip electrodes, and the voltage is measured between the RV ring and LV ring electrodes. The ratio of the measured voltage to the injected current then approximately represents the imped- ance between the distal end of the RV lead and the distal end of the LV lead. In both examples, the impedance vector passes through the LV chamber, thus the measured impedance is affected by the blood volume change of the LV. Clearly, it should be understood that LV impedance can also be measured by other electrode configurations, and that the different measurements can be combined in a weighted sum that serves a single parameter that is used by control unit 62 to determine optimal parameters of stimulation. Selection of various electrode configurations and thus a switching between different impedance measurements vectors can be achieved by switch matrix (not shown) that is arranged between impedance determination unit 70 and input terminals that are connected to individual electrodes. The switch matrix can be controlled by either impedance determination unit 70 or control unit 62.

Figure 11:
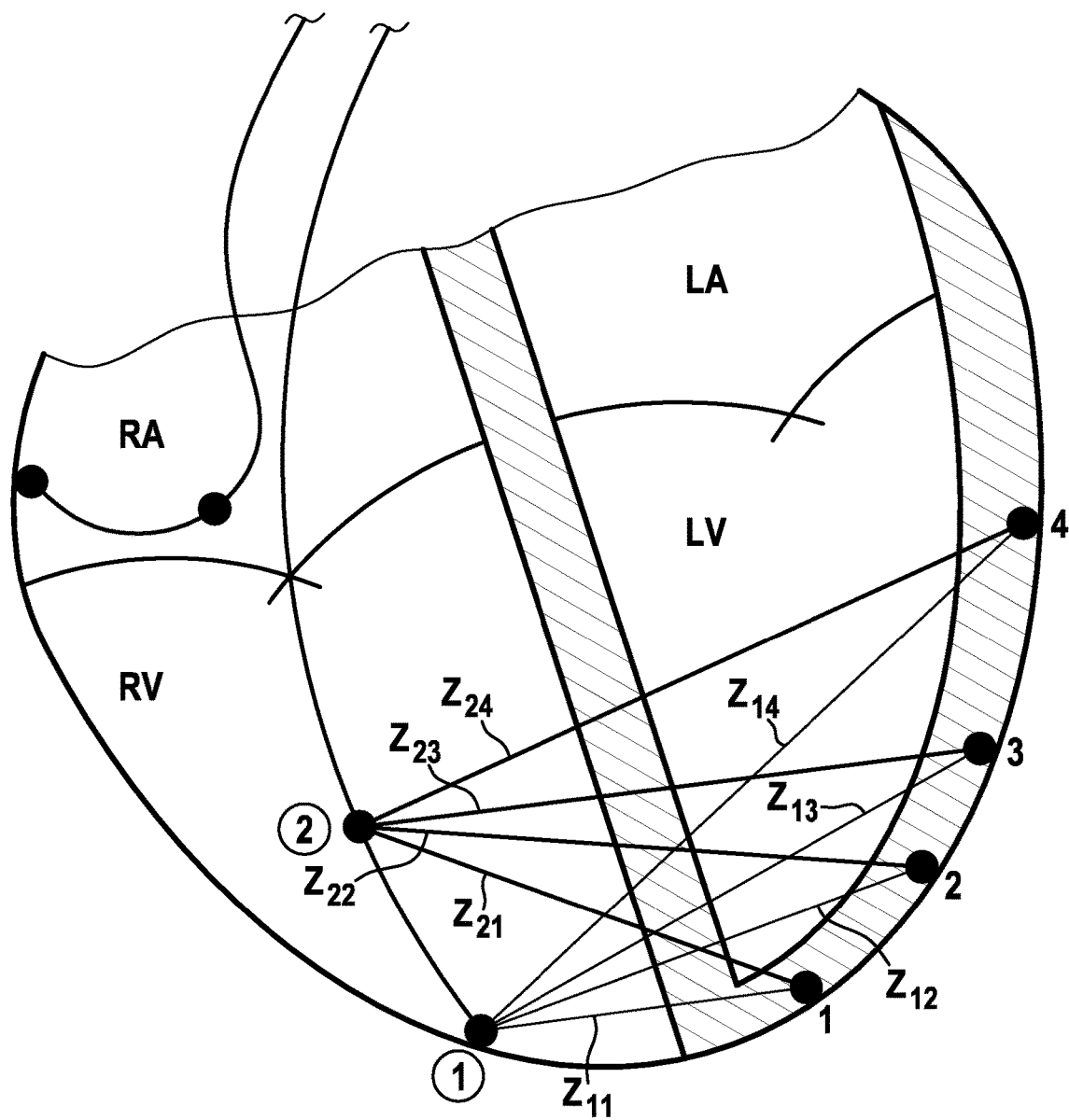
FIG. 11 is an illustration showing a number of possible impedance measurement vectors if the left ventricular electrode lead features four electrodes.

Reference is now made to FIG. 11 which illustrates a plurality of impedance measurement vectors that can be used to obtain a parameter for CRT optimization in the context of CRT-P or CRT-D devices. In such a device with a plurality of electrodes, a weighted sum of impedance measurements between the multiple electrodes can be used to create a single parameter that is used to calculate optimal parameters of stimulation. Stimulation parameters may include Stimulation mode (biventricular, left ventricular) amplitude, duration, timing between Stimulation pulse and intrinsic events or between a Stimulation pulse on one electrode and another (for instance between multiple electrodes within the heart). Stimulation parameters also include selection of a stimulation electrode which is being used or which combination of electrodes is being used and the timing between those used stimulation electrodes.

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

The following is a summary list of reference numerals and the corresponding structure used in the above description of the invention:
10 implantable medical device, pacemaker
12 heart
14 right atrial electrode lead
16 right ventricular electrode lead
18 right ventricular tip electrode
20 right ventricular ring electrode RV Ring
22 right atrial tip electrode RA Tip
24 right atrial ring electrode RA Ring
26 right atrium
30 left ventricular electrode lead
31 left ventricular ring electrode
32 left ventricular ring electrode
33 left ventricular ring electrode
34 left ventricular tip electrode
36 left ventricular defibrillation shock coil
28 right ventricle
38 ventricular defibrillation shock coil
40 atrial cardioversion shock coil
42 case
50 atrial stimulation pulse generator
52 right ventricular stimulation pulse generator
54 left ventricular stimulation pulse generator
56 atrial sensing stage
58 right ventricular sensing stage
60 left ventricular sensing stage 62 control unit
64 memory
66 telemetry circuit
68 activity sensor
70 impedance measurement unit
72 constant current source
74 voltage measuring unit
78 impedance evaluation unit
80 external device

The invention claimed is:

1. A biventricular implantable cardiac stimulator, comprising:
    a stimulation control unit;
    at least one stimulation unit;
    a contractility determination unit configured to generate a contractility signal reflecting myocardial contractility, said contractility determination unit being a closed-loop-stimulation sensor or a closed-loop-stimulation sensor system;
    said stimulation control unit being operatively connected to said stimulation unit to control delivery of stimulation pulses by said stimulation unit, said stimulation control unit is configured to switch between at least a univentricular left ventricular stimulation mode and a biventricular stimulation mode and to evaluate ventricular contractility in relation to a respective ventricular stimulation mode; and
    said contractility determination unit having or is connected to an impedance measurement unit and an impedance evaluation unit being configured to process an impedance signal received from said impedance measurement unit and generating the contractility signal based on an evaluated impedance that reflects the myocardial contractility, wherein said contractility determination unit is configured to generate the contractility signal reflecting myocardial contractility by evaluating a time course of the impedance signal and evaluating a first derivative of the impedance signal.

2. The biventricular implantable cardiac stimulator according to claim 1, wherein:
    said contractility determination unit is configured to perform a contractility evaluation of the contractility signal automatically; and
    said stimulation control unit is configured to switch between the univentricular left ventricular stimulation mode and the biventricular stimulation mode according to a result of the contractility evaluation.

3. The biventricular implantable cardiac stimulator according to claim 2, wherein said contractility determination unit is configured to perform contractility evaluations in a periodical manner.

4. The biventricular implantable cardiac stimulator according to claim 2, wherein the contractility evaluation is based on a comparison of the contractility signal with predetermined templates, wherein the predetermined templates include at least one template representing cardiac contractility values in the univentricular left ventricular stimulation mode and one template representing the cardiac contractility values in the biventricular stimulation mode.

5. The biventricular implantable cardiac stimulator according to claim 4, wherein the predetermined templates have the cardiac contractility values depending on heart rate.

6. The biventricular implantable cardiac stimulator according to claim 4, wherein said stimulation control unit is configured to determine the predetermined templates according to contractility evaluations, wherein the predetermined templates are updated in a periodical manner.

7. The biventricular implantable cardiac stimulator according to claim 1, wherein said stimulation control unit is configured to assess ventricular contractility based on the evaluated impedance signal and the respective ventricular stimulation mode.

8. The biventricular implantable cardiac stimulator according to claim 7, wherein said stimulation control unit is configured to generate data for a data structure that contains contractility signal values in association with stimulation mode identifier values that identify the respective ventricular stimulation mode that prevailed when a respective contractility signal value was determined.

9. The biventricular implantable cardiac stimulator according to claim 7, wherein the impedance signal reflects blood volume in a ventricle.

10. The biventricular implantable cardiac stimulator according to claim 1, wherein the contractility signal reflects dP/dt in a right and/or left ventricle.

11. The biventricular implantable cardiac stimulator according to claim 7, wherein:
    said impedance measurement unit and said impedance evaluation unit are configured to determine a plurality of impedance values between different pairs of electrodes connected or connectable to said impedance measurement unit; and
    said impedance evaluation unit is configured to generate left ventricular and right ventricular impedance signals reflecting left ventricular and right ventricular impedance values, respectively.

12. The biventricular implantable cardiac stimulator according to claim 11, wherein:
    said impedance evaluation unit is configured to generate evaluated left ventricular and right ventricular impedance signals that reflect left ventricular and right ventricular myocardial contractilities; and
    said stimulation control unit is configured to assess left and/or right ventricular contractility based on the evaluated impedance signal and the respective ventricular stimulation mode.

13. The biventricular implantable cardiac stimulator according to claim 1, wherein said stimulation control unit is configured to switch between the univentricular left ventricular stimulation mode and the biventricular stimulation mode depending on right and/or left ventricular contractility.

14. The biventricular implantable cardiac stimulator according to claim 1, further comprising:
    a memory for storing contractility signal values in association with stimulation mode identifier values that identify the respective ventricular stimulation mode that prevailed when a respective contractility signal value was determined; and
    a telemetry unit that is configured to enable an access to values in said memory by means of an external device.

* * * * *